(12) United States Patent
Wang et al.

(10) Patent No.: US 7,389,132 B2
(45) Date of Patent: Jun. 17, 2008

(54) MOLD-IN METHOD AND APPARATUS

(75) Inventors: Wei-Kung Wang, No. 14, Sublane 3, Lane 61, Section 2, Yen Chiu Yuan Road, Taipei (TW); Gin-Chung Wang, Taipei (TW)

(73) Assignee: Wei-Kung Wang, Nan Kang District, Taipei (TW)

( * ) Notice: Subject to any disclaimer, the term of this patent is extended or adjusted under 35 U.S.C. 154(b) by 884 days.

(21) Appl. No.: 10/752,437

(22) Filed: Jan. 6, 2004

(65) Prior Publication Data

US 2004/0210120 A1  Oct. 21, 2004

Related U.S. Application Data

(63) Continuation-in-part of application No. 09/766,237, filed on Jan. 19, 2001, now abandoned.

(30) Foreign Application Priority Data

Mar. 17, 2000  (TW) ............................. 89104938 A (51) Int. Cl.
*A61B 5/05* (2006.01)
*A61B 5/00* (2006.01)
(52) U.S. Cl. .................. 600/345; 600/347; 600/348; 600/310; 600/316; 600/365; 600/309
(58) Field of Classification Search ................ 600/300, 600/301, 309–366
See application file for complete search history.

(56) References Cited

U.S. PATENT DOCUMENTS 4,833,091 A * 5/1989 Leader et al. ............... 436/133
5,093,266 A * 3/1992 Leader et al. ................. 436/68
5,348,003 A 9/1994 Caro
5,351,685 A 10/1994 Potratz
5,782,757 A 7/1998 Diab et al.
5,836,317 A 11/1998 Kunst
5,836,883 A 11/1998 Tsuchiya et al.

(Continued)

FOREIGN PATENT DOCUMENTS

EP        623308 A1 *  11/1994

(Continued)

*Primary Examiner*—Charles A. Marmor, III
*Assistant Examiner*—Navin Natnithithadha
(74) *Attorney, Agent, or Firm*—Senniger Powers LLP (57) ABSTRACT

The present invention mainly relates to a method and apparatus for measuring the concentration of a solute in a solvent. Disclosed is an apparatus or method for determining the concentration of a solute in a solvent of a solution in a container having a time-varying volume by analyzing two signals received from the solution, comprising: measuring the quantity of the two received signals, converting the two signals into two electro-optical or electrical signals, performing a mathematical transformation on the two electro-optical or electrical signals, and determining the ratio of the transformation components of the two electro-optical or electrical signals. The present invention can be used in various applications of determining the ingredient concentration of a fluid, such as a gas or liquid. Particularly, the present invention finds applications in blood analysis in a human body for measuring, for example, the glucose, triglycerol, cholesterol, or oxyhemoglobin concentrations of the blood.

47 Claims, 2 Drawing Sheets

U.S. PATENT DOCUMENTS 6,078,833 A    6/2000  Hueber
6,289,230 B1   9/2001  Chaiken et al.
6,442,411 B1   8/2002  Guthermann

FOREIGN PATENT DOCUMENTS

| | | | |
|---|---|---|---|
| GB | 2361533 B | 10/2001 | |
| WO | 9846126 A1 | 10/1998 | |
| WO | 9960918 A1 | 12/1999 | |
| WO | 01025802 A2 | 4/2001 | |

\* cited by examiner

MOLD-IN METHOD AND APPARATUS

CROSS REFERENCE TO RELATED APPLICATIONS

The invention of the present application is a continuation in part of U.S. patent application Ser. No. 09/766,237, filed on Jan. 19, 2001 now abandoned.

The corresponding applications of the present invention in R.O.C. (Taiwan) are pending under R.O.C. Patent Application No. 88106056, entitled "METHOD AND APPARATUS TO MEASURE BLOOD INGREDIENTS BY PULSATILE MICRO-CIRCULATION," filed on 5 May 1999, and R.O.C. Patent Application No. 89104938, entitled "MOLD-IN METHOD AND APPARATUS," filed on 17 Mar. 2000, both by the same inventor as the present invention.

FIELD OF INVENTION

The present invention relates to a method and apparatus for measuring the concentration of a solute in a solvent. The invention can be used in various applications of determining the ingredient concentration of a fluid, such as a gas or liquid. Particularly, the present invention finds applications in blood analysis in a human body for measuring, for example, the glucose, triglycerol, cholesterol or oxyhemoglobin concentrations of the blood.

BACKGROUND AND SUMMARY OF INVENTION

While measuring the concentration of a specific solute in a solvent, all we need to know is the ratio of the solute to the solvent. If there are two solutes and one concentration of the two solutes is known, all we need to know is the ratio between two solutes and the concentration of the other solute can be thus calculated. There are various situations requiring the determination of concentrations, such as air quality studies, water quality studies and chemical factory product monitoring. Among others, the studies of clinical diagnostics utilize lots of concentration measurements including measuring the concentrations of glucose, triglycero, cholestride, hemoglobin ureic acid, and oxyhemoglobin. Other possible measurements include the microorganisms such as specific virus, bacteria or its maker or toxin in a human body fluid, especially the blood. Additionally, in enzyme activity studies concerning immuno-tests to antibodies or antigens (such as hormones and enzymes), it is needed to analyze the product of the enzymes or the product of the coupled reactions, the antigen-antibody complex or the labels on the antigen-antibody complex, antigen-enzyme hormone can be protein. Particularly, their concentrations are needed to be determined.

As mentioned before, the concentration of ingredient B in a solution A can be defined to be the ratio of B with respect to the solvent in the solution A. For example, the concentration of glucose (i.e., the ingredient) in blood can be defined as the ratio of glucose with respect to the water in blood.

Although the definition of concentration is clear and straightforward, there exit many problems in putting the measurements of concentrations of solutions into practice. One of the challenges confronted is to measure a solute in a solution in a small time-varying and signal-generating volume in a large stationary container. The time-variance of the volume infers that the volume of the solution or just a volume that contained signal sources. What is in the volume can be liquid, air, condensed matter or ionic solution or a combination of it, being measured is not fixed with respect to time and/or space. The signal generation refers to measuring methods that involve introducing signals into the volumes and the concentration of the signal source can thus be determined by analyzing the induced signal. The problem is that the induced signal will always be mixed up with noise produced by the stationary container and thus, the analyzed result will be hardly accurate. For example, when an infrared light source is directed to a finger of a human body and toward to the blood sample inside the vessel of the finger, both the absorption peaks of water and glucose will show up, together with a lot of scattering noise mainly caused by non-blood stationary sources. Apparently, the noise is detrimental to the accuracy of concentration measurements.

Thus there is a need to provide an apparatus and method for accurately and effectively measuring the concentration of a signal source in a volume. This invention addresses the need.

In one aspect of the invention, there is a method (Mold-In strong method, which means two signals are in a mold-like relationship strongly) for determining a ratio of two signals $A(t)$ and $B(t)$ based on two real signals $A'(t)$ and $B'(t)$ including noise $N_A(t)$ and $N_B(t)$, respectively, wherein:

$$N_A(t) \approx N_B(t),$$

$$A'(t) = A(t) + N_A(t),$$

$$B'(t) = B(t) + N_B(t), \text{ and}$$

$$A(t) = K_0 * B(t), K_0 > 1,$$

said method comprising the steps of: (a) performing a mathematical transformation T on both $A'(t)$ and $B'(t)$; and (b) estimating $K_0$ from the following relation:

$$F_i[A'(t)]/F_i[B'(t)] \approx K_0,$$

where $F_i$ is the $i^{th}$ order component of the transformation T; and (c) determining the ratio of two signals $A(t)$ and $B(t)$ from the estimated $K_0$.

In another aspect of the invention, there is a method (Mold-In medium method, which means two signals are mold-like in a medium way) for determining a ratio of two signals $A(t)$ and $B(t)$ based on two real signals $A(t)$ and $B(t)$ mixed with noise $N_A(t)$ and $N_B(t)$, respectively, wherein:

$A'(t)$ is statistically confident to be not noisy such that $N_A(t) \approx 0$, $$A'(t) = A(t) + N_A(t) \approx A(t),$$

$$B'(t) = B(t) + N_B(t), \text{ and}$$

$$A(t) = K_0 * B(t),$$

said method comprising the steps of:
(a) performing a mathematical transformation T on both $A'(t)$ and $B'(t)$; and (b) estimating $K_0$ from the following relation:

$$F_i[A(t)]/F_i[B'(t)] \approx K_0,$$

where $F_i$ is the $i^{th}$ order component of the transformation T and the position of $F_i [B'(t)]$ is identified by the noise around $F_i [A(t)]$; and (c) determining the ratio of two signals $A(t)$ and $B(t)$ from the estimated $K_0$.

In a further aspect of the invention, there is a method (Mold-In week method, which means two signals are in a weak mold-like relationship) for determining a ratio of two signals A'(t) and B'(t) based on two signals A(t) and B(t) mixed with noise $N_A(t)$ and $N_B(t)$, respectively, wherein:

A'(t) is a less noisy signal;

$$A'(t)=A(t)+N_A(t),$$

$$B'(t)=B(t)+N_B(t), \text{ and}$$

$$A(t)=K_0*B(t),$$

comprising the steps of:
(a) identifying the minimum of B'(t), $B'(t)_{min}$, by A'(t); and
(b) removing the static noise by $[B'(t)-B'(t)_{min}]$.

In yet another aspect of the invention, there is an apparatus for determining the concentration of a solute in a solvent of a solution in a container having a time-varying volume by analyzing two signals received from the solution, comprising: a detector for measuring the quantity of the two received signals; a signal converter for converting the two signals into two electro-optical signals; and means for determining a ratio of the two electro-optical signals by performing the above-mentioned mold-in methods.

In yet another aspect of the invention, there is an apparatus for measuring the concentration of a solute in a solvent of a solution in a container having a time-varying volume by analyzing two signals received from the solution, comprising: a pressure source for generating the volume change of the time-varying volume; a detector for detecting the two received signal; a signal converter for converting the two received signals into two electrical signals; and means for determining a ratio of the two electrical signals by performing the above-mentioned mold-in methods.

In yet another aspect of the invention, there is an apparatus for measuring the blood pressure variation $[P(t)-P(t)_{diastolic}]$ in a human body by a marker signal B'(t) in the blood of the body, comprising: a detector for measuring the marker signal B'(t); and a data processing unit determining the $[P(t)-P(t)_{diastolic}]$ based on $[B'(t)-B'_{min}(t)]$, where:

P(t) is blood pressure as function of time,
$P(t)_{diastolic}$ is diastolic pressure or minimum of P(t), and
$B'_{min}(t)$ is the minimum of the marker signal B'(t).

BRIEF DESCRIPTION OF DRAWINGS

The present invention now will become better understood with regard to the accompanying drawings in which.

DETAILED DESCRIPTION OF INVENTION

The present invention is based on an important recognition that the induced signal from a solvent is mixed with the same noise as the induced signal from the ingredient is. Taking the blood for example, the induced signal from water is mixed with the noise that is the same as the noise mixing with the induced signal from glucose. The same noise is also mixed with the induced signals from other ingredients such as triglycero, cholestride, ureic acid, oxyhemoglobin. As mentioned above, the volume of solution to be measured is time-varying and denoted as V(t), the induced signal from a solute B is denoted as B(t), and the induced signal from the solvent is denoted as A(t). In an ideal situation without any noise involved in, A(t) and B(t) are in proportion with each other as follows:

$$A(t)=K_0*B(t); \text{ where, } K_0>>1 \quad (1)$$

Apparently, if the $K_0$ is known, the concentration of B (i.e., $1/K_0$) is known, too. However, in the real world, the actually measured induced signals of both solvent and solute, respectively denoted as A'(t) and B'(t), will include noise $N_A(t)$ of the solvent A and noise $N_B(t)$ of the solute B and satisfy:

$$A'(t)=A(t)+N_A(t); \text{ and} \quad (2)$$

$$B'(t)=B(t)+N_B(t). \quad (3)$$

Now, a mathematical transformation F is applied to both sides of equations (2) and (3) such that:

$$F_i[A'(t)]=F_i[A(t)+N_A(t)]; \text{ and} \quad (4)$$

$$F_i[B'(t)]=F_i[B(t)+N_B(t)]; \quad (5)$$

where $F_i$ represents any component of the mathematical transformation.

Assume $N_A(t) \approx N_B(t)$, and in fact, $N_A(t)$ and $N_B(t)$ are generally stationary with respect to time t, and thus, we may choose a more dynamic component $F_i$ of the transformation, in order to ensure that:

$$F_i[N_A(t)] \approx F_i[N_B(t)] \approx 0; \quad (6)$$

That is because the stationary noise $N_A(t)$ and $N_B(t)$ will appear to be negligible at the dynamic order of the mathematical transformation.

Under the condition of (6), equations (4) and (5) can further be simplified by:

$$F_i[A'(t)] \approx F_i[A(t)]; \text{ and} \quad (7)$$

$$F_i[B'(t)] \approx F_i[B(t)]; \quad (8)$$

Now, in combination of equation (1), the valuable estimation:

$$F_i[A'(t)]/F_i[B'(t)] \approx K_0. \quad (9)$$

There are many linear transformations that can be used here, such as Fourier, Danbechies, and Mexican hat. Under any linear transformations, equations (4) and (5) can be further written as follows:

$$F_i[A'(t)]=F_i[A(t)+N_A(t)]=F_i[A(t)]+F_i[N_A(t)]; \text{ and} \quad (4')$$

$$F_i[B'(t)]=F_i[B(t)+N_B(t)]=F_i[B(t)]+F_i[N_B(t)]; \quad (5')$$

where, $F_i$ is any component of the transformation.

As mentioned above, the present invention is based on recognition that in most cases, the induced signal from a solvent is mixed with the same noise as is the induced signal from the ingredient. Thus, let $N_A(t)=N_B(t)=N(t)$, after dividing above equation (4') by equation (5'), a further result can be obtained:

$$F_i[A'(t)]/F_i[B'(t)]=K_0-(K_0-1)*\{F_i[N(t)]/(F_i[B(t)]+F_i[N(t)])\}, \text{ and } K_0>>0. \quad (10)$$

Since $K_0>>0$ and $F_i[N(t)]>0$, the largest value of equation (10) is $K_0$. The largest value of $F_i[A'(t)]/F_i[B'(t)]$ for all possible i is the best possible approximation for $K_0$. It should be noted that the best approximation of $K_0$ may appear for several different $F_i$ s. The number of appearing times of the best approximation is one of the indications for how good the approximation is.

For most practical applications, the time-varying volume V(t) of the solution is a periodic function. If we use the Fourier transformation, from the Fourier transform of one cycle, we can calculate the first harmonics of A'(t), B'(t) and N(t). In general, the relationship $F_I[N(t)] << F_I[B'(t)] << F_I[A'(t)]$ holds true due to the nature of the solution, and equation (9) can be applied as:

$$F_I[A'(t)]/F_I[B'(t)] \approx k_0 \qquad (11)$$

If $F_I[N(t)]$ is not very small in comparison with $F_I[B'(t)]$, we may interpret the noise level around the $F_I[A'(t)]$, a large and clean signal than can distinguish itself from the noise by interpolation. Then the following equation:

$$F_I[B(t)] = F_I[B'(t)] - F_I[N(t)]_{estimated}, \qquad (12)$$

can be used to estimate $F_I[B(t)]$.

However, since $F_I[A'(t)]$ is a large and clean signal distinguishing itself from the noise through interpolation, the noise level may be interpreted around the $F_I[A'(t)]$ and $F_I[N(t)]$ is actually negligible. Then, $K_0$ can be estimated by the following equation:

$$K_0 \approx F_I[A(t)]/F_I[B(t)] \qquad (13)$$

The above-mentioned method is very useful to estimate the ratio $K_0$ of the two signals from the solvent and solute, and both signals are following each other like a mold. The method is referred to as a Mold-In method, and more specifically, a Mold-In strong method.

In a general system, N(t) mainly results from the larger portion of the volume that is stationary with respect to time t, while A(t) and B(t) mainly result from the small portion of the volume that is time-varying. The useful Mold-In method of the present invention can be better understood from the following embodiment.

If the absorption spectrum is used onto a finger of a human body to measure the concentration of glucose or other solute in the blood of the body. The bone, muscle, skin or hair of the body can be viewed as the constant parts that do not vary with time. Only the blood in the artery varies its volume according to the pressure cycle. During the systolic, the blood volume is largest; and during the diastolic, the blood volume is smallest. The amount of glucose and water in the finger will change accordingly. Let us designate the glucose signal with B(t) and the water signal with A(t). N(t) is the noise and is mainly resulted from the static part of the finger. When the Fourier transform is applied to N(t), the N(t) will be confined to near zero frequency, that is, N(t) merely appears some value around its $0^{th}$ harmonic. According to equation (11), the Fourier transformation of both the A'(t) (measured water signal) and B'(t) (measured glucose signal) will reveal the concentration of the glucose through the ratio of the first harmonic of A'(t) and B'(t). As mentioned before, if the N(t) is still measurable around the first harmonic of B'(t), the exact position of the first harmonic can be identified by the first harmonic of A'(t), which is a much larger quantity. The estimation of N(t) at the position the first harmonic can thus be found by interpolation with the noise around, according to equations (12) and (13). Actually, this approach can also be applied to higher harmonics for obtaining $K_0$. Other methods for improving a signal, such as higher intensity of the exciting source, more precise wave length, and longer sampling time, can be used in combination with the Mold-In method of the present invention to obtain a better estimation of $K_0$.

As mentioned in the first paragraph of BACKGROUND AND SUMMARY OF THE INVENTION, if there are two signal sources and one concentration of the two signal sources is known, all we need to know is the ratio between these two and the concentration of the other signal sources solute can be thus calculated. For example, from the strength of the water signal, the equivalent amount of water can be calculated; and from the strength of the solute signal (e.g., the glucose), the equivalent amount of the solute can be calculated. As a result, from the ratio $K_0$, the glucose concentration in water and therefore, in the blood, can be calculated because the ratio between water and blood can be easily obtained.

The Mold-In method can also be used in all kinds of clinical diagnosis, such as an enzyme test or immuno test, by measuring the specific signals from the samples. The signals could be induced signals such as a light absorption, fluorescence, light scattering and optic rotation. They could also be emanations such as radiations from radioisotopes, chemi-luminescences, or auto-luminescences. Since the measured solution is in an elastic container, the effective volume of the signal producing solution can be expressed as a function of the pressure. In other words, the applied pressure can be used to represent the signal from the solution: A(t). The signal producing solution has a volume V(t) that can be controlled from the applied pressure (i.e., A(t)). It should be noted that the pressure is just one possible way to produce a change in the controlled effective volume. Other moving compartment could also be used to construct the A(t). As mentioned before, $$B'(t) = B(t) + N(t), \text{ and}$$

$$A(t) = K_I B(t), \text{ where N(t) is the noise.}$$

From the second equation, if A(t) is proportional to V(t), B(t) will also be proportional to V(t).

We may also use one component of the transformed A(t) and B'(t), to seek the largest value of:

$$F_i[K_1 B(t)]/F_i[B(t) + N(t)],$$

for all i.

The best approximation of $K_1$ can thus be obtained, and it may appear in several different components in accordance with several different transformations. The accuracy of $K_1$ may further be confirmed. The relation between $K_1$ and the concentration of the specific product can be measured by using the similar instrument. Then, let the solution have different concentrations of the specific solute, measure the specific signal from each solute, and compare with the applied pressure A(t).

Similarly, the signal from the solvent (e.g., water) may be measured to find out the $K_1$ for water. The mold-in (strong) is then used to find the $K_0$ between water and solute, and $K_1$ is found for the specific solute.

The two groups of signal A(t) and B(t) are similar to a mold. However, if there is not any relation between the noise, it is referred to as Mold-In medium.

Figure 1:
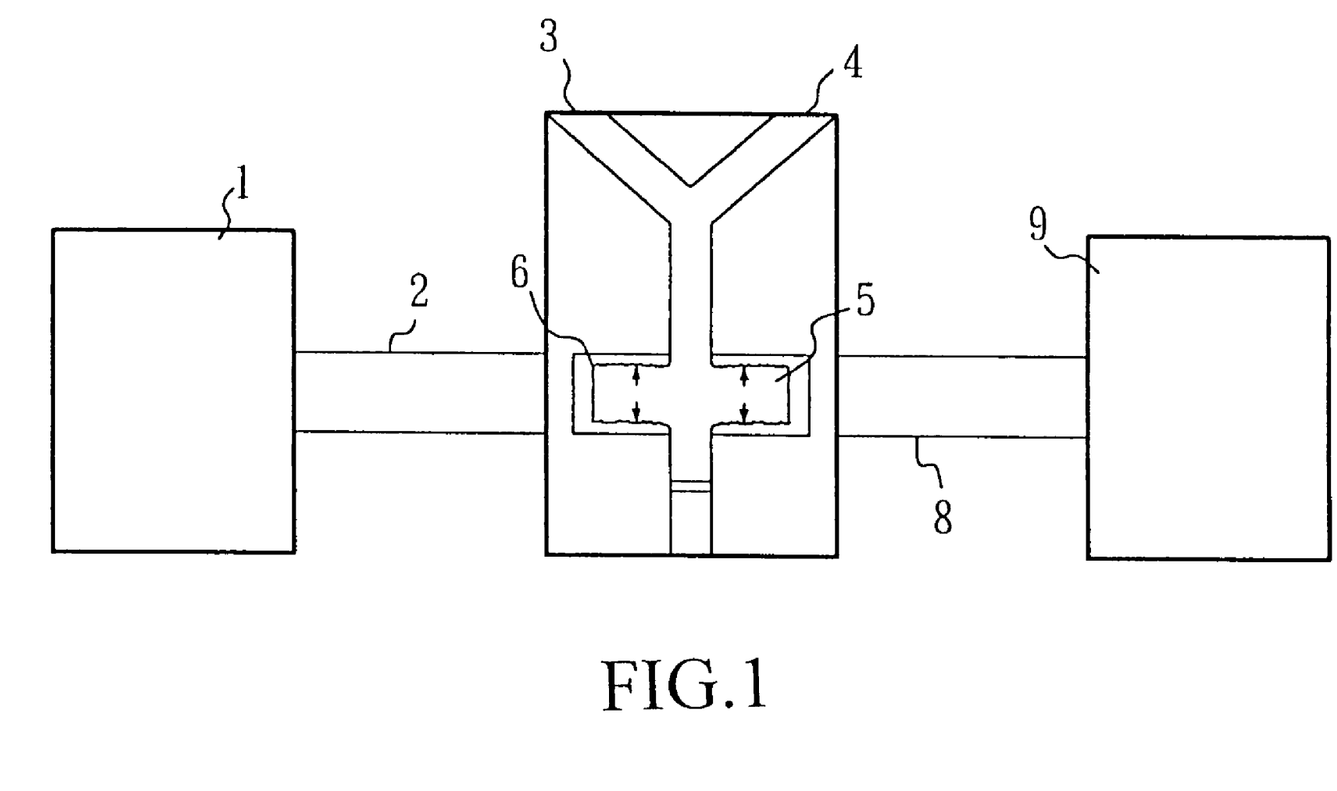
FIG. 1 shows an exemplary mechanical apparatus using the mold-in methods of the present invention to measure the concentration of a sample to be tested.

The present invention is described below with reference to the accompanying drawings. FIG. 1 shows a mechanical apparatus using the mold-in methods of the present invention to measure the concentration of a sample to be tested. A light source 1 is used to provide the exciting light signal required for the apparatus, and the light source 1 is preferably, a laser (e.g., a diode laser). A light (or signal) guide 2, such as an optical fiber, may be used to lead the exciting signal toward a sample 5; however, the light guide 2 is optional and particularly, while using a laser as the light source 1, the light guide could be omitted. The sample 5 is the product by mixing a tested substance 3 and a reagent 4, and is confined within a container 6 formed by some elastic material and having an effective volume V(t). Then the pressure P(t) may be applied by a pressing device 7 to the sample 5 to introduce a change of the effective volume V(t) and as a result, the optical volume of the sample 5 could be changed. Let A(t) denote the signal representing the optical volume of the sample 5, and B(t) denote the signal related to the signal of water or other solvent as a marker. A light collection device 8 such as a lens or optical fiber is provided to collect the output signals. A detector 9 is used for detecting the collected signals and the detected signals are denoted as A'(t) and B'(t), which are comprised of two signals A(t) and B(t) mixed with noise $N_A(t)$ and $N_B(t)$, respectively. Examples of the detector 9 include an InGeAs detector for infrared signals, Si detector for visible and ultraviolet signals or a photo multiplier.

As mentioned above, the Mold-in methods of the present invention can be used to determine the ratio between the signals A(t) and B(t) and the concentration of the tested substance 3 can thus be obtained from the concentration of the product 5.

The Mold-In methods of the present invention are useful in any man made machine such as perfusion, incubation system and especially the [MEMS (micro-electro-mechanic system)]. The system can be used to measure very small volume of the sample in-situ and does not have to transfer the sample into another container for detection. In general, P(t) is selected to be proportional to V(t) and thus, the concentration of the specific substance in the sample 5 can be calculated from B'(t) of the sample. Preferably, P(t) may be selected as a periodic function to enhance the resolution, for example, a trigonometric function such as $\cos\omega t$ or $\sin\omega t$.

Figure 2:
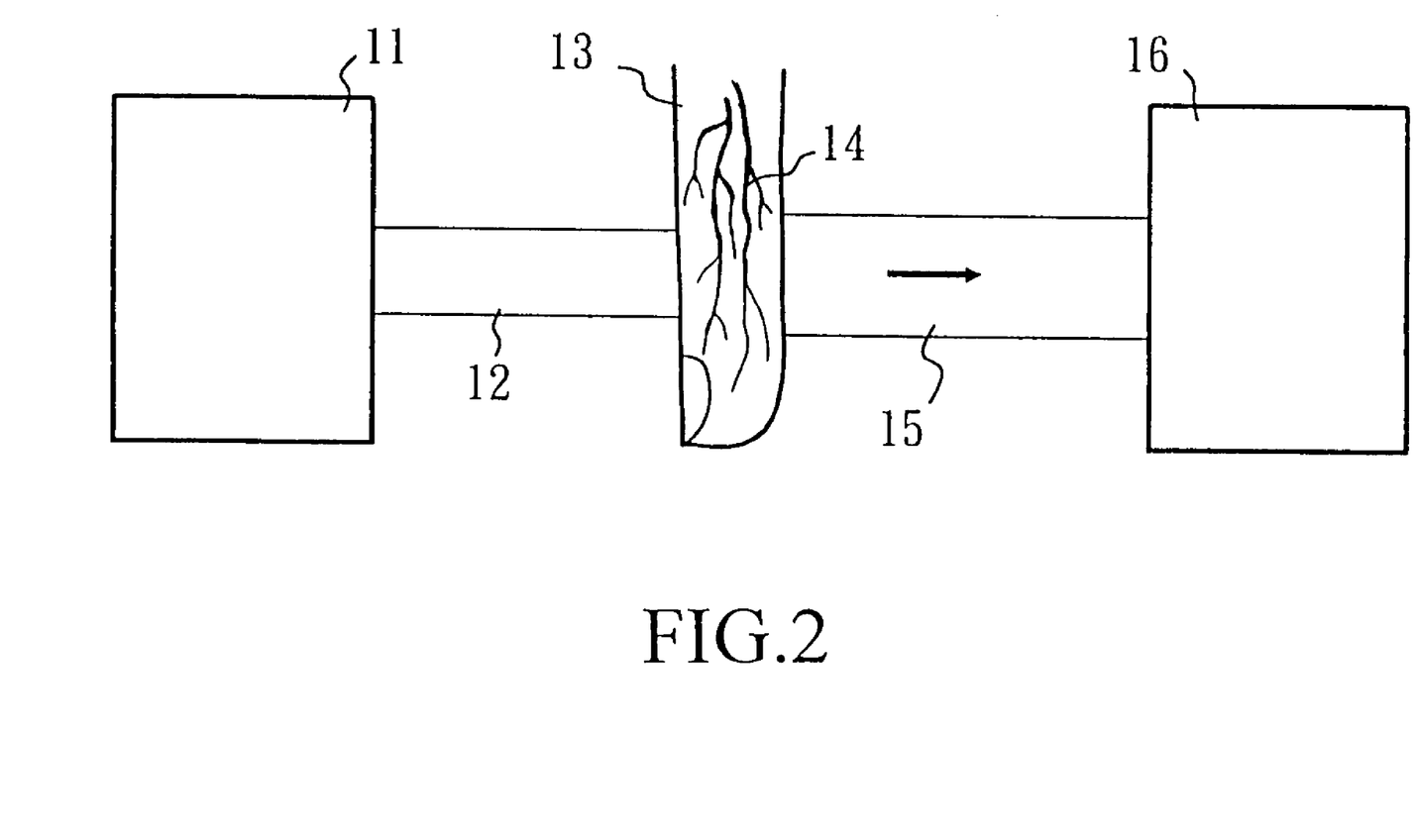
FIG. 2 shows a non-invasive blood analysis apparatus using the mold-in methods of the present invention to measuring, for example, at a finger, the glucose concentration of the blood in a human body.

The above methods of the present invention can also be used to measure the solute concentrations in the tissue either in the living body or outside of body in a man-made machine and the liquid can be artificially made instead of natural blood. FIG. 2 shows a non-invasive blood analysis apparatus using the mold-in methods of the present invention to measuring, for example, at a finger 13, the glucose concentration of the blood in a human body. Like the apparatus in FIG. 1, the blood analysis apparatus comprises a light source 11, a light guide 12, a light collection device 15 and a detector 16. Under normal blood pressure, the blood volume in the artery 14 is proportional to the blood pressure, because the artery is like an elastic container that under normal blood pressure follows the Hook's law: V(t)=C*P(t), where C is the bulk modulus. The ration of the two signals A(t) and B(t) can be obtained by using the mold-in methods of the present invention so long as the signals A(t) and B(t) are varied in accordance with the applied pressure. This volume can also be in a perfused tissue, or incubation medium with cell or tissue culture.

Actually, the above methods may be used in a reversed way by measuring the B'(t) for the solvent (i.e., water) of the blood or a solute with very strong signal (e.g., hemoglobin), to track the A(t). Following this way, the photo-electric method may be used to measure the pulse. All the algorithms disclosed in the U.S. Pat. No. 5,730,138 owned by the applicant and published on 24 Mar. 1998 can thus be used to diagnose the blood circulation. Since artery is everywhere in the body, especially organs, such as brain, liver, lung, spleen and etc., this relation can also be used to map the change of C (bulk modulus) due to malignant.

The measurements of the above methods are not limited to be applied onto fingers. They may also be used to other parts of a human body, even used to internal organs. The only requirement is to lead the source signal to the part of body that has artery, for example, through the channels of the endoscope or any signal that can be generated by the volume no matter it is from a marker in the blood such as radioactive isotope or auto luminescent tag etc. that emanates signals or from the specific signal induced by the interaction of the source signal with the blood in the tissue, the concentration of a specific ingredient as well as elasticity of a pixie in the internal organ from its specific signal may be estimated. However, those body parts with extrusive shape will be more convenient for the measurements.

The source signal can be electromagnetic waves including γ-ray, x-ray, ultra-violet, visible, infra-red, far-infrared, or even microwave. Electrical signals could be of impedance. Radiation could be as positron, β-ray or α-particle, etc. Mechanical signals could be ultrasound or sound wave. The infra-red, far-infrared absorption, scattering or optical rotation are the most commonly used signals.

In pharmaco-kinetics, the above methods can also be used to monitor the concentration of some drug in the blood, as long as there is a specific signal for the drug. This can be done non-invasive either in situ or in vitro.

The annealing is used to identify a single strain DNA or RNA. These can be measured by ultra-violet adsorption. The enlargements of molecular complexes including also the antibody-antigen reaction to form antigen-antibody complex can also be measured by light scattering at different angle with respect to the incident light (i.e., Nephelometer). The methods can also be used to analyze the signal from markers which are labeled on, for example, antibody for anneled double strain DNA and antibody-antigen complex such as radiation (i.e., radio-immunoassay), fluorescence (fluorescence-immunoassay), or absorption. The signal is treated as B(t), and the changed effective signal producing volume as A(t). The methods may then be used to estimated the best $K_1$ to study the condition of the reaction.

While using the methods of the present invention, A(t) not only is limited to be from the pressure, but also can be any ways that are able to change the effective signal producing volume V(t) in a systematic way. From A(t), the V(t) can be calculated.

The Mold-In (medium) method can also be used in the situation that A'(t) and B'(t) are from two different signals having different noise. For example, one of them is from an induced signal and the other is from emanation.

If A(t) and B(t) are closely related functions with the same period, and both the measured A'(t) and, especially B'(t), have large noise, the noise is mainly resulted from the stationary sources. From the maximum and minimum of A(t), the minimum of B(t) can thus be found.

From A'(t), from the conditions $B(t_2)=B_{min}(t)$, and $N(t) \approx N(t_2)$ at all t (because it is stationary), a $t_2$ can be identified.

The noise may be eliminated from the stationary source by:

$B'(t)-B_{min}(t_2) \approx B(t)-B(t)_{stationary}$. $B(t)-B(t)_{stationary}$ becomes a much clearer signal. Then from:

$$\text{Max }[B'(t)-B'_{min}]/\text{Max }[A'(t)-A'(t_2)], \qquad (a)$$

where, $B'_{min}$ is the measured minimum $B(t)_{min}$, and at $t_{min}=t_2$, A'(t) is minimum.

The equation (a) can be used to estimate the concentration of a specific solute in the solution that generates the specific signal B(t).

The equation (a) can be approximated by the first harmonic of Fourier transform ($F_1$):

$$F_1[B(t)]/F_1[A(t)]. \qquad (b)$$

The method is referred to as Mold-In weak. The Mold-In weak can be used to study any A'(t) and B'(t) with correlated maximum and minimum, while B'(t) has noise from stationary sources.

When B'(t) is not clearly measured, B'(t)$_{min}$ can be identified by following the A'(t). This method is extraordinary useful when B'(t) is periodic. If the t$_{min}$ is known, by signal averaging, a clear B(t)$_{min}$ is obtained.

Some working examples are illustrated as follows.

Case I.

Let A(t) denotes the blood pressure signal, and B(t) denotes the blood signal that flows out of the blood vessel, which can be measured by, for example, the laser Doppler flow meter. As mentioned in the Mold-In medium method, the blood pressure wave can be monitored by a specific signal from one ingredient in the arterial blood such as the absorption signal of water or hemoglobin. Therefore, a light source may be used to monitor the pressure by the waveform. Another light source, which may be the same one as the above, is used to monitor the blood flow by the Doppler signal. Therefore, from the ratio:

$K_P = [F_{max} - F_{min}]/[P_{max} - P_{min}]$, where $F_{max}$ is the maximum blood flow;
$F_{min}$ is the minimum blood flow;
$P_{max}$ is the maximum blood pressure; and
$P_{min}$ is the minimum blood pressure, the efficiency of blood perfusion can be expressed.

The value $K_P$ may be approximated by:

$F_I[F(t)]/F_I[A(t)]$, where $F_I$ is the first harmonic of Fourier transform.

The above coefficient $K_P$ is very important in diagnosis hypertension, diabetes. A lower $K_P$ implies that a poor perfusion efficiency can be caused by diabetes and is one of the main causes for hypertension.

Case II.

From the blood pressure wave monitored by the specific signal in the arterial blood, the best time to deliver drug into the human body can thus be determined. During the systolic, a large amount of blood is pumped into the artery, as well as tissues. Meanwhile, if the drug, such as antibiotic, hormone or nutrient is injected into the body at this moment, the mixing of the drug with the blood stream will be maximized. This will also cause less trauma due to the injection which may be caused by toxication, or osmotic effect of high concentration of the drug, or just sudden increase of internal pressure to hide the normal blood flow, and the efficiency of distributing the drug into the whole body can thus be improved.

The above method can be incorporated into every injection device. The injected drug, no matter through a needle or an air presser, can be delivered at the peak of the systolic pressure. A lade injection can be divided into several cardiac cycle. Conventional injection at the bottom or arm of a human body for the reason of much muscle needs some modification. The injection may be performed at the body parts having the largest blood perfusion, for example, palms or feet. The blood pressure monitor can have other forms such as a pressure sensor or EKG.

Case III.

The combination of the glucose detection with the above injection controlling device can comprise an artificial pancreas. The Mold-In strong using water signal and glucose signal from infrared absorption or scattering identifies the glucose concentration. At the same time, we may have $P(t)-P(t)_{min}$ to monitor if the glucose is above certain level. This measurement can be done as frequently as is required because it is non-invasive.

The insulin can be injected through an injection system. According to the blood pressure, a very small amount is injected through a micro-tube or air pressure at each systolic pressure. This artificial pancreas will be as good as a natural one. The similar idea can be applied to many other artificial organs.

Case IV.

The above-mentioned glucose detection system can also be integrated into the communication system, with each handset equipped with, for example, a glucose sensor, uric acid, cholesterol, triglyceride, or blood pressure sensor. The blood components and the blood pressure of a person may be measured by the telephone handset, and the measured information can be transmitted through the communication system toward the doctor or any persons who will take medical care of the person. If the doctor would like to know the patient's physical conditions, only a phone call is needed to obtain all the data. In other words, the physical examination on the patient can be done on the phone, and the examination data can be further transferred to the doctor's database for later use.

Case V.

This invention can also be used in a reverse way. Use the A'(t) or V'(t) and the measured P'(t): pressure to find out the C by CP(t)=V(t). If C is significantly changed, it means the elasticity change in this specific pixie $V=V(X_0,Y_0,Z_0)$ in the larger volume V(X,Y,Z) the C can be compared with the C of $V_N(X_0,Y_0,Z_0)$ (normal value from average samples that stored in the processor) to find out of the elasticity is changed at $V=V(X_0,Y_0,Z_0)$, or the $V(X_0,Y_0,Z_0)$ is compared with $V(X+\Delta x, Y+\Delta y, Z+\Delta z)$, $\Delta x$, $\Delta y$, $\Delta z$ is the size of a pixie to find out of $V(X_0,Y_0,Z_0)$ is abnormal due to diseases such as malignant, arteriosclerosis.

Case VI.

Even if the volume of the man-made volume changing container is not in a good linear elasticity range, that is, the bulk modulus is not constant, the method still can be used to estimate the concentration of a solute in the container, as mentioned in Case V. If the volume is precisely known, the Mold-In medium algorithm can be applied. If there is another marker, the Mold-In strong algorithm can be used.

From the invention thus described, it will be obvious that the embodiments and description are not intended to limit the invention. The invention may vary in many ways. Such variations are not to be regarded as a departure from the spirit and scope of the invention, and all such modifications, as would be obvious to one skilled in the art, are intended for inclusion within the scope of the following claims.

What is claimed is:

1. An apparatus for analyzing parameters in a volume with V=V(t), where t is time, said volume comprising a plurality of substances; the apparatus comprising:

a first signal source A=A(t), said first signal source being representative of a first substance comprising the volume;

a second signal source B=B(t), said second signal source being representative of a second substance comprising the volume with $A(t)=B(t)K_0$, where $K_0>1$, $V(t)=B(t)K_1$, where $K_0$, $K_1$ are stationary in a time interval $t_0$, where $t_0$ is any real value; and a first detector to measure a first signal assigned as C'(t) according to the time interval $t_0$, where C'(t) can be either V'(t) related to the volume by $V'(t)=V(t)+N_V(t)$ or A'(t) related to the first signal source by $A'(t)=A(t)+N_A$ (t), wherein $N_A(t)$ is the noise of A(t), and $N_V(t)$ is the noise of V(t) during the measurement time interval $t_0$, a second detector to measure a second signal assigned as B'(t) according to a time interval $t_0$, where B'(t) is related to the second signal source by B'(t)=B(t)+$N_B$(t), wherein $N_B$(t) is the noise of B(t) during the measurement time interval $t_0$, wherein the first and second signals C'(t) and B'(t) are transferred into electro optical signals by a signal converter and sent into a data processor to analyze either $K_0$ for determining the concentration of the second substance with respect to the first substance or $K_1$ for determining the concentration of the second substance with respect to the volume.

2. An apparatus as claimed in claim 1 wherein V=V(t) comprises:

an additional property of V(t)=K2P(t), where P(t) is the pressure in V(t), K2 is stationary in the time interval t0, and t0 is any real number; and detectors to measure P'(t)=P(t)+$N_P$(t), wherein $N_P$(t) is the noise of P(t) during the measurement time interval $t_0$, to transfer the measured B'(t) and P'(t) into electro-optical signal and send the signal into a data processor to analyze $K_2$.

3. An apparatus as claimed in claim 2, wherein the concentration of B is calculated from $K_2$.

4. An apparatus as claimed in claim 2, wherein the elasticity of V(t) is calculated from $K_2$.

5. An apparatus as claimed in claim 4, wherein the V is a pixie of V(x,y,z), a much larger volume.

6. An apparatus as claimed in claim 5, wherein the V(x,y,z) is compared with V(x+$\Delta$x,y+$\Delta$y,z+$\Delta$z) in which $\Delta$x, $\Delta$y, $\Delta$z are the size of the pixie.

7. An apparatus as claimed in claim 5, wherein the V(x,y,z) is compared with Vs(x,y,z) a stored value in the processor.

8. An apparatus as claimed in claim 2, wherein the $t_m$ is found at which V($t_m$)=V at maximum volume from A(t) or P(t).

9. An apparatus as claimed in claim 8, wherein the V($t_m$) is guiding the injection of an ingredient into V at $t_m$.

10. An apparatus as claimed in claim 9, further comprising an ingredient detector for injecting another ingredient in accordance with the result of the detector.

11. An apparatus as claimed in claim 10, wherein said ingredient comprises glucose and said another ingredient comprises insulin.

12. An apparatus as claimed in claim 2, wherein $K_2$ is used to analyze the concentration of B.

13. An apparatus as claimed in claim 2, wherein one of the P'(t) or C'(t) is assigned as L'(t), said data processor analyze the original data B'(t) and E'(t) by the following steps:

performing a mathematical transformation T on both E'(t) and B'(t);

estimating $K_R$ from the following relation: $F_i[E'(t)]/Fi[B'(t)] \approx K_R$, R:0, or 1, or 2 accordingly where $F_i$ is the $i^{th}$ order component of the transformation T; and determining the ratio of two signals E(t) and B(t) from the estimated $K_R$.

14. An apparatus as claimed in claim 13, wherein the mathematical transformation T is linear, said processor further performing the steps of:

identifying and estimating $F_i[N_B(t)]$ by the noise around $F_i[E(t)]$; and determining the estimated $K_R$ from the following relation:

$$\{F_i[E'(t)]-F_i[N_B(t)]\}/\{F_i[B'(t)]-F_i[N_B(t)]\} \approx K_R.$$

15. An apparatus as claimed in claim 13, the processor further performing the step of:

approximation $K_R$ from the largest value of Fi[E'(t)]−Fi[NB(t)] for all kinds of linear transformation T and all possible orders of the transformation T, based on the following relation:

$$\{F_i[E'(t)]-F_i[N_B(t)]\}/\{F_i[B'(t)]-F_i[N_B(t)]\} \leq K_R.$$

16. An apparatus as claimed in claim 13, wherein

E'(t) is statistically confident to be not noisy such that $N_E(t) \approx 0$,

E'(t)=E(t)+$N_E \approx$E(t),

B'(t)=B(t)+$N_B$(t), and

E(t)=$K_R$*B(t), said method comprising the steps of:

performing a mathematical transformation T on both E'(t) and B'(t);

estimating $K_R$ from the following relation:

$$F_i[E'(t)]/Fi[B'(t)] \approx KR$$

where Fi is the $i^{th}$ order component of the transformation T and the position of Fi[B'(t)] is identified by the noise around $F_i$[E'(t)]; and determining the ratio of two signals E(t) and B(t) from the estimated $K_R$.

17. An apparatus as claimed in claim 16, wherein the mathematical transformation T is linear, further comprising the steps of:

identifying and estimating $F_i[N_B(t)]$ by the noise around $F_i[E(t)]$, and denoting the estimating of $F_i[N_B(t)]$ to be $F_i[N_E(t)]$; and estimating $K_R$ from the following relation:

$$F_i[E(t)]/\{F_i[B'(t)]-F_i[N(t)]\} \approx K_R.$$

18. An apparatus as claimed in claim 17, further comprising the steps of:

approximation $K_R$ from the largest value of Fi[E'(t)]−Fi[NB(t)] for all kinds of linear transformation T and all possible orders i of the transformation T, based on the following relation:

$$F_i[E(t)]/\{F_i[B'(t)]-F_i[N(t)]\} \leq K_R.$$

19. An apparatus as claimed in claim 13, wherein the transformation T is Fourier transform.

20. An apparatus as claimed in claim 19, wherein the $F_i$ is $F_1$, the first harmonic of the Fourier transform.

21. An apparatus as claimed in claim 13, wherein the step for determining a ratio of two signals E(t) and B(t) based on two real signals E'(t) and B"(t) including noise $N_E$(t) and $N_B$(t), respectively, wherein:

E'(t) is a least noisy signal;

E'(t)=E(t)+$N_E$(t),

B'(t)=B(t)+$N_B$(t), and

E(t)=$K_R$*B(t), comprising the steps of:

identifying the minimum of B(t), B'(t)$_{min}$, by E'(t); and removing the static noise by [B'(t)−B'(t)$_{min}$].

22. An apparatus as claimed in claim 21, further comprising the steps of approximating $K_R$ by using the following relation:

$$\text{Maximum of } [E(t)-E(t)_{min}]/\text{Maximum of } [B(t)-B(t)_{min}] \approx K_R,$$

where E(t)$_{min}$ and B(t)$_{min}$ are the minimum of E(t) and B(t), respectively.

23. An apparatus as claimed in claim 21, further comprising the steps of approximating $K_R$ by using the following relation:

$$F_i[E(t)-E(t)_{min}]/F_i[B'(t)-B(t)_{min}] \approx K_R,$$

where both E(t) and B(t) are periodic and $E(t)_{min}$ and $B(t)_{min}$ are the minimum of E(t) and B(t), and $F_i$ is the $i^{st}$ order of a transformation.

24. An apparatus as claimed in claim 13, wherein the volume comprises blood, the blood pressure is measured by signal E'(t).

25. An apparatus as claimed in claim 24, further comprising a instrument for measuring the blood flow F'(t) in the volume, and means for determining $K_p$, which is an indicator of perfusion efficiency, based on the following relation: $F(t)=K_p E(t)$.

26. An apparatus as claimed in claim 2, wherein the volume change in a periodic way.

27. An apparatus as claimed in claim 1, wherein a signal source comprises hemoglobin.

28. An apparatus as claimed in claim 1, wherein $K_0$ or $K_1$ is used to analyze the concentration of B.

29. An apparatus as claimed in claim 1, wherein the signal comprises induced signal.

30. An apparatus as claimed in claim 29, wherein the signal comprises and electromagnetic wave.

31. An apparatus as claimed in claim 29, wherein the induced signal comprises mechanical wave.

32. An apparatus as claimed in claim 1, wherein a signal source in the volume comprises a marker.

33. An apparatus as claimed in claim 1, wherein the volume comprises blood.

34. An apparatus as claimed in claim 1, wherein the volume comprises tissue.

35. An apparatus as claimed in claim 1, wherein a signal source comprises uric acid.

36. An apparatus as claimed in claim 2 further comprises a pressure source for generating the volume change.

37. An apparatus as claimed in claim 1, wherein volume change in a periodic way.

38. An apparatus as claimed in claim 1, wherein signal is transmitted through communication.

39. An apparatus as claimed in claim 1, wherein the volume is in a man-made system.

40. An apparatus as claimed in claim 1, wherein the signal source comprises DNA.

41. An apparatus as claimed in claim 1, wherein the signal source comprises RNA.

42. An apparatus as claimed in claim 1, wherein the signal source comprises protein.

43. An apparatus as claimed in claim 1, wherein the signal source comprises colored molecular.

44. An apparatus as claimed in claim 1, wherein the signal source comprises glucose.

45. An apparatus as claimed in claim 1, wherein the signal source comprises cholesterol.

46. An apparatus as claimed in claim 1, wherein the signal source comprises triglycerol.

47. An apparatus as claimed in claim 1, wherein the signal source comprises enamation.

\* \* \* \* \*